United States Patent [19]

Schneider et al.

[11] Patent Number: 4,973,473

[45] Date of Patent: Nov. 27, 1990

[54] SKIN CARE PREPARATION

[75] Inventors: Emil Schneider, Long Branch; James J. Ferone, Bridgewater, both of N.J.

[73] Assignee: Revlon, Inc., New York, N.Y.

[21] Appl. No.: 370,468

[22] Filed: Jun. 23, 1989

[51] Int. Cl.$^5$ ................. A61K 7/021; A61K 7/48
[52] U.S. Cl. ............................ 424/63; 514/8; 514/844; 514/847; 514/848; 514/873; 514/944; 252/315.01
[58] Field of Search ............... 424/63, 70, 78; 514/844–848, 873, 944, 8; 252/315.01

[56] References Cited

U.S. PATENT DOCUMENTS

| | | | |
|---|---|---|---|
| 3,766,267 | 10/1973 | Zak et al. | 564/201 |
| 3,855,290 | 12/1974 | Zak et al. | 564/159 |
| 4,014,995 | 3/1977 | Juliano et al. | 514/783 |
| 4,108,849 | 8/1978 | Thomas | 530/825 |
| 4,126,142 | 11/1978 | Saute | 424/78 |
| 4,303,676 | 12/1981 | Balazs | 514/773 |
| 4,335,103 | 6/1982 | Barker et al. | 424/81 |
| 4,416,873 | 11/1983 | Puchalski et al. | 251/129.21 |
| 4,438,095 | 3/1984 | Grollier et al. | 424/70 |
| 4,482,537 | 11/1984 | El-Menshawy et al. | 424/59 |
| 4,488,564 | 12/1984 | Grollier et al. | 424/71 |
| 4,488,564 | 12/1984 | Grollier et al. | 132/202 |
| 4,582,865 | 4/1986 | Balazs et al. | 524/29 |
| 4,636,524 | 1/1987 | Balazs et al. | 514/781 |
| 4,663,159 | 5/1987 | Brode, II et al. | 424/70 |
| 4,837,019 | 6/1989 | Georgalas et al. | 424/60 |
| 4,869,897 | 9/1989 | Chatterjee et al. | 424/63 |

OTHER PUBLICATIONS

"Cosmetics–Science and Technology", vol. 1, 2nd Ed., John Wiley & Sons, Inc., New York, N.Y., 1972, Ch. 2.

*Primary Examiner*—Merrell C. Cashion, Jr.
*Assistant Examiner*—Amy Hulina
*Attorney, Agent, or Firm*—Donald T. Black; Julie Blackburn

[57] ABSTRACT

This invention provides skin care compositions which include an emollient complex containing a primary moisturizing agent selected from certain carboxylic acid amides and a mucopolysaccharide secondary moisturizing agent. The compositions also include one or more skin-structuring proteins and an astringent agent which confers skin-firming characteristics. Long lasting protection is afforded by the optional incorporation of a cellulosic film-former. Preferred embodiments take the form of two discrete gel phases.

18 Claims, No Drawings

SKIN CARE PREPARATION

This invention is in the field of body-treating compositions. The invention is directed especially to products for conditioning the skin, particularly preparations which both emolliate and astringe the skin.

BACKGROUND OF THE INVENTION

Human beings have been conscious of and concerned about the condition and appearance of their skin since the beginnings of recorded history. Skin which appears wrinkled, discolored, rough, flabby, or malformed gives an unwanted impression to others. Consequently, from the earliest times, various treatments and adornments have been employed to enhance the complexion one presents to the world.

A prime cause of skin wrinkling and roughness is dehydration of the scarf skin, especially the stratum corneum. Studies have shown that dryness and reduced flexibility of the stratum corneum can be corrected by rehydrating the skin, water being the only substance that will plasticize the stratum corneum effectively. Consequently, a number of skin care creams and lotions have appeared which contain agents to moisturize the skin.

The skin dehydration problem and the use of emollients to correct it are discussed in "Cosmetics—Science and Technology," Vol. 1, 2nd Ed., John Wiley & Sons, Inc., New York, NY, 1972, Ch. 2. The emollients used in skin care products include both film-forming materials which lubricate and coat the skin to passively impede evaporation of moisture and materials which are hygroscopic and actively attract moisture to the skin, i.e., humectants.

It is known that hydrocarbon, silicone and vegetable oils emolliate the skin, primarily by forming an occlusive film, a barrier to moisture loss. Skin care compositions containing such oils are disclosed, for example, in U.S. Pat. No. 4,488,564.

On the other hand, various polyhydric organic compounds, e.g., certain hydroxy-alcohols, esters, and amides, function primarily as humectants. Among the amides with known skin moisturizing abilities are various derivatives of gluconamide, as described, for example, in U.S. Pat. Nos. 3,766,267 and 3,855,290.

Mucopolysaccharides comprise another class of polyhydric organic compounds which may be employed as moisturizing agents in skin care compositions. More specifically, the use of hyaluronic acid or derivatives thereof in skin care compositions is disclosed in U.S. Pat. Nos. 4,303,676, 4,582,865 and 4,636,524, for example.

In addition to moisturizing agents of the sort described above, skin care formulations may contain various proteinaceous materials which are substantive to the skin and tend to smooth and soften the skin by becoming an integral part thereof or forming a film thereon. These materials include hydrolyzed animal protein, as disclosed in U.S. Pat. Nos. 4,416,873 and 4,482,537, for example. Protein having a vegetable origin can be used as well, oat flour being disclosed in U.S. Pat. No. 4,014,995.

Although the available skin care compositions may contain at least one skin moisturizing component and, perhaps, some protein, complete skin care requires attention to several additional problems, problems not satisfactorily addressed by the skin care compositions heretofore available. One of these problems is poor skin tone, i.e., sagging, flabby skin. The inclusion of a moisturizer and substantive protein in a skin care product may actually accentuate this condition, i.e., to the extent the product is taken up by the skin and leads to puffiness. Another problem is presented by the fact that benefits of using many of the known skin care preparations are short-lived; the emphasis is on treating a present skin condition, little attention being given to preventing the problem from soon recurring.

In addition, a number of the water-soluble materials useful as moisturizers are incompatible with candidate protein components, which makes it difficult to produce an attractive homogeneous product. This invention is directed toward solving the aforesaid problems.

Consequently, it is one object of this invention to provide skin care preparations which include both moisturizer and skin-structing protein, but which avoid incompatibility. It is another objective to provide preparations which also improve the tone and firm the skin. Yet another objective is to provide skin care products which are useful, not only for treating a present skin condition, but also to protect the skin against recurrence of the condition.

SUMMARY OF THE INVENTION

The skin care compositions within the scope of this invention include an emollient complex containing both a primary moisturizing agent selected from carboxylic acid amides and a mucopolysaccharide secondary moisturizing agent. In addition, the compositions contain a skin-structuring protein component, as well as an astringent agent. Preferred compositions also include a cellulosic film-former. Especially desirable embodiments include more than one separate phase.

DETAILED DESCRIPTION

The emollient complex employed in the skin care compositions of this invention includes both primary and secondary moisturizing agents. As used herein, the terms "primary" and "secondary" convey no implications as to relative importance.

The primary moisturizing agent includes a skin-humectating carboxylic acid amide or salt thereof. A number of such amides are known, amides having pendant hydroxyl groups being especially efficacious in this regard. Some of the most useful such amides are aliphatic hydroxycarboxylic acid amides containing at least 6 carbon atoms. Gluconamides, especially N-substituted gluconamides, are very effective; among such compounds methoxypropyl gluconamide, disclosed in U.S. patent application No. 07/184,858, filed Apr. 22, 1988, is preferred.

The secondary moisturizing agent is selected from that class of compounds known as mucopolysaccharides. In the context of this application, the term "mucopolysaccharide" is confined to those naturally-occurring, high molecular weight polymers whose molecular structures contain disaccharide repeating units. For example, the repeating units can be the N-acetylchondrosine structure, as found in chondroitin sulfate, or the alternating beta 1-3 glucuronidic and beta 1-4 glucosaminidic repeating unit found in hyaluronic acid. Derivatives of hyaluronic acid, e.g., salts and hydrolysis products thereof, are very effective.

In addition to the primary and secondary moisturizing agents, the skin care compositions of this invention optionally may include other moisturizing ingredients.

Examples of such ingredients include various hydroxylated compounds, such as monomeric glycols, e.g., propylene glycol, glycerin and butylene glycol, but polymeric moisturizers may also be used, such as those including polyglycerylmethacrylate.

The compositions of this invention also include a skin-structuring protein component. The term "skin-structuring protein" as used herein is intended to include natural proteins derived from animal or marine sources, as opposed to plant or vegetable sources, and which are substantive to the skin. Such animal proteins include, for example, high molecular weight glycoproteins, such as the fibronectins. Other useful animal proteins include soluble collagen, hydrolyzed animal collagen, striated muscle fiber or an extract thereof, hydrolyzed or partially hydrolyzed elastin, hydrolyzed silk, and soluble reticulin. The skin-structuring protein component can comprise a mixture, as well as a single protein product.

The skin care compositions within the scope of this invention also include one or more astringent agents. Such agents include, for example, arnica flowers or extracts thereof, lower alkyl alcohols, boric acid, lactic acid, methol, camphor, zinc phenol sulphonate, and zinc chloride or sulfate. For many purposes, a natural product, e.g., arnica extract, is preferred, especially in combination with a proteinaceous material, such as hydrolyzed marine protein and/or a vegetable protein as can be extracted from barley and other grains, for example.

The compositions of this invention preferably include a cellulosic film-former, but this component is not required. Cellulosic film-formers include polysaccharides such as chitin, which can be obtained from marine sources. The chemical structure of the cellulosic film-former component is distinguished from that of the mucopolysaccharide component in predominately containing monosaccharide repeating units, N-acetyl-D-glucosamine in the case of chitin.

In addition to the elements described above, the skin care compositions of this invention may also include cosmetically acceptable preservatives, colorants, fragrances, masking agents, and carriers, such as water and lower alkyl, i.e., $C_1$–$C_4$, alcohols, including ingredients to control the viscosity of the compositions.

The quantities of the various ingredients in a composition within the scope of this invention can be varied over a wide range, it only being necessary that cosmetically effective amounts be present. In general, the primary moisturizing agent will comprise between about 0.25 and about 10 percent, desirably between about 0.3 and about 5 percent, by weight of the composition. The entire polysaccharide content, including both those having disaccharide and those having monosaccharide repeating units, will comprise between about 0.2 and about 2 percent, preferably between about 0.1 and about 0.5 percent, by weight of the composition. The skin-structuring protein will comprise between about 0.05 and about 8 percent, desirably between about 0.05 and about 2.0 percent, by weight of the composition. The astringent agent, e.g., arnica combined with marine and vegetable protein, will comprise between about 0.1 and about 5 percent, preferably between about 0.1 and about 0.25 percent, by weight of the composition.

In the following Examples the compositions comprise two discrete gel phases. The first gel is transparent, colorless, and contains predominantly water-soluble elements; the second phase is colored and opaque. A decorative aspect may be introduced by extruding the second gel as a discrete structure into the first gel.

EXAMPLE 1

| Ingredient | Amount (% by wt.) |
| --- | --- |
| Colorless Gel | |
| Methoxypropylgluconamide | 0.5 |
| Sodium Hyaluronate, Chitin[5] | 0.25 |
| Propylene Glycol | 4.0 |
| Glycerin | 1.0 |
| Butylene Glycol | 3.0 |
| Polyglycerin Methacrylate, and Propylene Glycol[1] | 7.2 |
| Chitin Extract[2] | 4.0 |
| Acrylic Acid Polymer[3] | 35.0 |
| Triethylamine | 1.67 |
| PEG-40 Hydrogenated Castor Oil | 0.8 |
| Methyl Paraben | 0.15 |
| Trisodium EDTA | 0.05 |
| Imidazolidinyl Urea | 0.3 |
| Fragrance | 0.05 |
| Water q.s. | 100.00 |
| Colored Gel | |
| Sodium Hyaluronate, Chitin[5] | 0.5 |
| Propylene Glycol | 6.0 |
| Striated Muscle Fiber | 0.01 |
| Hydrolyzed Animal Elastin and Soluble Reticulin[6] | 0.2 |
| Soluble Animal Collagen, Glutaral, Propylene Glycol[7] | 1.0 |
| Fibronectin | 0.5 |
| Chitin Extract[2] | 5.0 |
| Arnica Extract[4] | 2.0 |
| Acrylic Acid Polymer[3] | 28.3 |
| Triethylamine | 1.46 |
| PEG-40 Hydrogenated Castor Oil | 1.2 |
| Guanine, Water, Isopropyl Alcohol, Methyl Cellulose[8] | 5.0 |
| Methyl Paraben | 0.15 |
| Trisodium EDTA | 0.05 |
| Imidizolidinyl Urea | 0.3 |
| Titanium Dioxide | 3.0 |
| Fragrance | 0.15 |
| Water q.s. | 100.0 |

[1]Available as LUBRAJEL from Friedman Industries, P.O. Box 415, Tuckahoe, NY 10707.
[2]Available as ACTIGLOW - C from Active Organics, 7715 Densmore Ave., Van Nuys, CA 91406.
[3]2.5% CARBOMER 940 from BF Goodrich Co., 6100 Oak Tree Blvd., Cleveland, OH 44131. By weight dissolved in water.
[4]Obtained as FIRMOGEN LS 3797 from Laboratories Serobiologiques, Somerville, NJ. Also contains barley extract and hydrolyzed animal protein.
[5]Available as ACTIGLIDE from Active Organics, Van Nuys, CA 91406.
[6]Obtained from Croda, Inc., 183 Madison Ave., New York, NY 10016 as RETICUSOL.
[7]Available from Croda, Inc. as COLLASOL.
[8]MEARLMAID AA obtainable from Mearl Corp., 41 East 42nd Street, New York, NY 10017.

EXAMPLE 2

| Ingredient | Amount (% by wt.) |
| --- | --- |
| Colorless Gel | |
| Same as Example 1 | |
| Colored Gel | |
| Sodium Hyaluronate, Chitin[5] | 0.5 |
| Propylene Glycol | 6.0 |
| Striated Muscle Fiber | 0.01 |
| Hydrolyzed Animal Elastin and Soluble Reticulin[6] | 0.2 |
| Soluble Animal Collagen, Glutaral, Propylene Glycol[7] | 1.0 |
| Fibronectin | 0.5 |
| Chitin Extract[2] | 5.0 |
| Arnica Extract[4] | 2.0 |
| Acrylic Acid Polymer[3] | 28.3 |
| Triethylamine | 1.46 |

-continued

| Ingredient | Amount (% by wt.) |
| --- | --- |
| PEG-40 Hydrogenated Castor Oil | 1.2 |
| Guanine, Water, Isopropyl Alcohol, Methyl Cellulose[8] | 9.0 |
| Methyl Paraben | 0.15 |
| Trisodium EDTA | 0.05 |
| Imidazolidinyl Urea | 0.3 |
| Titanium Dioxide | 1.5 |
| Red Iron Oxide Extender, Talc, Propylene Glycol | 1.125 |
| Fragrance | 0.15 |
| Water q.s. | 100.0 |

Footnotes:
See Example 1.

What is claimed is:

1. Skin treatment compositions comprising:
   0.25–10% of a primary moisturizing agent selected from gluconamides containing at least 6 carbon atoms;
   0.2–2% of a mucopolysaccharide moisturizer containing disaccharide repeating units;
   0.05–8% of a skin-structuring protein selected from the group consisting of glycoproteins, collagen, striated muscle fiber, elastin, and reticulin; and
   0.1–5% of an astringent agent selected from the group consisting of arnica flowers or extracts hereof, methanol, lower alkyl alcohol, boric acid, lactic acid, methol, camphor, zinc phenol sulphonate, and zinc chloride or sulfate; in a cosmetically acceptable carrier.

2. The composition of claim 1 further containing a cellulosic film-former wherein the mucopolysaccharide moisturizer and cellulosic film former together comprise 0.2–2% of the total composition.

3. The compositions of claim 1 wherein said gluconamide is methoxypropyl gluconamide.

4. The compositions of claim 1 wherein said mucopolysaccharide moisturizer includes hyaluronic acid.

5. The compositions of claim 1, wherein said glycoprotein is fibronectin.

6. The compositions of claim 1 wherein said astrigent agent is arnica.

7. The compositions of claim 6 further comprising a proteinaceous material which is vegetable protein or hydrolyzed animal protein.

8. The compositions of claim 2 wherein said cellulosic film-former is a polysaccharide having monosaccharide repeating units.

9. The compositions of claim 2 wherein said cellulosic film-former includes chitin.

10. The compositions of claim 1 wherein said carrier is an aqueous gel.

11. The compositions of claim 1 wherein said carrier comprises two separate gel phases, a first phase and a second phase.

12. The compositions of claim 11 wherein said primary moisturizing agent is present only in said first phase, whereas said skin-structuring protein is present only in said second phase.

13. The compositions of claim 11 wherein one of said phases is colorless and the other is colored.

14. The compositions of claim 11 wherein one of said phases is transparent and the other is opaque.

15. The composition of claim 1 wherein said primary moisturizing agent comprises between 0.3 and about 5 percent by weight of the composition.

16. The compositions of claim 1 wherein the total polysaccharide comprises between about 0.1 and about 0.5 percent by weight of the composition.

17. The compositions of claim 1 wherein said skin-structuring protein comprises between about 0.05 and about 2.0 percent by weight of the composition.

18. The composition of claim 1 wherein said astringent agent comprises between about 0.1 and about 0.25 percent by weight of said composition.

* * * * *